United States Patent [19]
Vroom

[11] 4,397,958
[45] Aug. 9, 1983

[54] HYDROCARBON ANALYSIS

[75] Inventor: Theo Vroom, Huizen, Netherlands

[73] Assignee: The Foxboro Company, Foxboro, Mass.

[21] Appl. No.: 300,154

[22] Filed: Sep. 8, 1981

[51] Int. Cl.³ .................... G01N 25/20; G01N 31/12; G01N 33/22

[52] U.S. Cl. .................................. 436/141; 422/62; 422/78; 364/497; 364/499; 436/8; 436/160

[58] Field of Search ....... 23/230 PC, 230 A, 230 HC; 422/78, 62; 364/497, 499

[56] References Cited

U.S. PATENT DOCUMENTS

| | | | |
|---|---|---|---|
| 3,463,613 | 8/1969 | Fenske et al. | 23/230 PC |
| 3,531,255 | 9/1970 | Fenske et al. | 23/230 PC |
| 3,533,745 | 10/1970 | Fenske et al. | 23/230 PC |
| 3,582,280 | 6/1971 | Fenske | 23/230 PC |
| 3,582,281 | 6/1971 | Fenske et al. | 23/230 PC |
| 4,248,599 | 2/1981 | Mommessin et al. | 23/230 HC |

Primary Examiner—Michael S. Marcus
Attorney, Agent, or Firm—Andrew T. Karnakis

[57] ABSTRACT

Analysis of hydrocarbon mixtures to determine desired characteristics, particularly a determination of octane number of gasolines, undergoing partial oxidation/cool flame reactions. Pre-analysis performed on a target fuel sample of known composition and octane number is utilized to arrive at an optimum point of the reaction, a point believed to represent a condition where a maximum of the fuel is oxidized during the reaction. In the preferred embodiment disclosed, the optimum point is the reactor block temperature that generates a maximum peak temperature rise of the cool flame reaction of the target fuel. This optimum reactor temperature is utilized in further analyses of other known samples to develop a matrix of peak temperature rise versus time to reach peak coordinates. Any unknown fuel sample whose peak amplitude/time coordinate is within the matrix is compared with matrix values to determine its octane number as well as an indication of its composition. The overall arrangement is embodied in a microprocessor controlled octane analyzer suitably interconnected with a refinery process stream to provide continuous on-line octane number monitoring.

12 Claims, 10 Drawing Figures

HYDROCARBON ANALYSIS

FIELD OF THE INVENTION

This invention relates generally to the analysis of hydrocarbon mixtures, and more particularly to a determination of octane number and composition of unknown hydrocarbon-containing substances utilizing partial oxidation techniques.

BACKGROUND OF THE INVENTION

The phenomena of stabilized "cool flame" reactions wherein a mixture of hydrocarbon vapor and air is maintained at pressure and temperature conditions below that of an explosive reaction is well understood in the art. Particularly, for several years now, it has been known that certain measurable parameter values of a cool flame reaction involving the oxidation of a hydrocarbon mixture can be correlated to some characteristic of the hydrocarbon sample, specifically the octane rating for gasoline.

One such prior technique is disclosed in U.S. Pat. No. 3,738,810, which teaches that, when a gasoline is oxidized in a cool flame reaction, either the time elapsed between injection of the sample and the beginning of the reaction or the severity of the reaction (e.g., the peak height of the reaction) directly correlates with the octane number of that gasoline sample as determined by certified analysis by accepted ASTM methods on the combustible fuel research (CFR) engine. Such apparatus and method have achieved a degree of commercial success, due in part to the relatively low purchase and installation costs, ease of maintenance, and repeatability of measured values as compared to the current standard against which all octane rating numbers are based, i.e., the CFR engine.

Although the techniques disclosed in the aforementioned patent have been successfully demonstrated in a commercial device that works well in its intended application, it does suffer from certain drawbacks. For example, the device disclosed, being primarily analog, is subject to inaccuracies and slow response times as well as problems in interfacing with digital process control units commonly employed in today's chemical processing plants and refineries to provide highly accurate automatic regulation over the entire process. However, perhaps the most notable deficiency of this and other similar analyzers is their inability to perform on-line blending with process streams of widely varying composition without frequent recalibration with CFR engine rated standards. In the specific example of gasoline production, present analysis techniques allow on-line measurement of a particular, a priori defined, hydrocarbon blend. For example, during certain stages in the gasoline refining process, reformates are produced whose octane rating and consistency are known within well defined, narrow limits. Hence, although these prior art techniques make reference to the ability of performing "blending" operations, this form of blending referred to is limited in scope to constituents of small composition deviations and moreover occurs after considerable resources have been expended in the refining process. Accordingly, it represents a more expensive, less flexible operation.

Therefore, notwithstanding the usefulness of the prior art hydrocarbon analyzers operating with cool flame reactors, a need still exists for a highly accurate device capable of automatically blending mixtures containing widely varying compositions that is inexpensive and simple to operate and easily adapted to continuous on-line operation and computerized process management and control applications. This is especially true in a petrochemical refining process wherein large amounts of energy are required to produce a fuel of known composition and octane rating.

SUMMARY OF THE INVENTION

One aspect of the present invention involves the discovery that for a "target" hydrocarbon composition (i.e., a product which is ultimately desired to be produced) there exists an optimum operating point for the reaction. In the preferred embodiment, this optimum point is the reactor block temperature within the cool flame region that generates a maximum peak temperature rise of the cool flame/partial oxidation reaction for that target composition. It is thought that this optimum point results in a condition under given conditions where a maximum of the components of the substance are consumed by the cool flame reaction.

The preferred embodiment of the invention discloses a microprocessor controlled octane analyzer suitably adapted to provide continuous on-line octane number monitoring of refinery process streams of varying composition. In this manner the analyzer output can serve as an input to an automatic blender to produce gasoline derivatives and target fuel compositions of desired octane number. The analyzer includes an explosion-proof heated steel block, i.e., the reactor block, having an inner cavity in which the cool flame reaction takes place. After gasoline sample and an air mixture are injected into the cavity under controlled conditions, an exothermic reaction occurs whose peak temperature and time to reach the peak is measured. In accordance with the invention, the optimum reactor block temperature is determined by injecting a sample of known fuel whose octane number is at the mid-point of the range of interest and then varying the reactor block temperature while other samples of the same known fuel are run through the analyzer. The optimum temperature is then that temperature which generates the maximum peak. This optimum reactor temperature is utilized in further analyses as the basis for developing a matrix of peak amplitudes versus the time to reach peak amplitude for groups of fuels of equal octane numbers but of widely varying composition. Means are provided within the microprocessor to then determine an indication of the composition as well as the octane number for any unknown hydrocarbon samples whose peak amplitude versus the time to reach peak measurement is within the matrix.

BRIEF DESCRIPTION OF THE DRAWINGS

Other aspects, advantages, and objects of the present invention will become more apparent from the following detailed description read together with the accompanying drawing figures wherein.

DESCRIPTION OF THE PREFERRED EMBODIMENT

Figure 1:
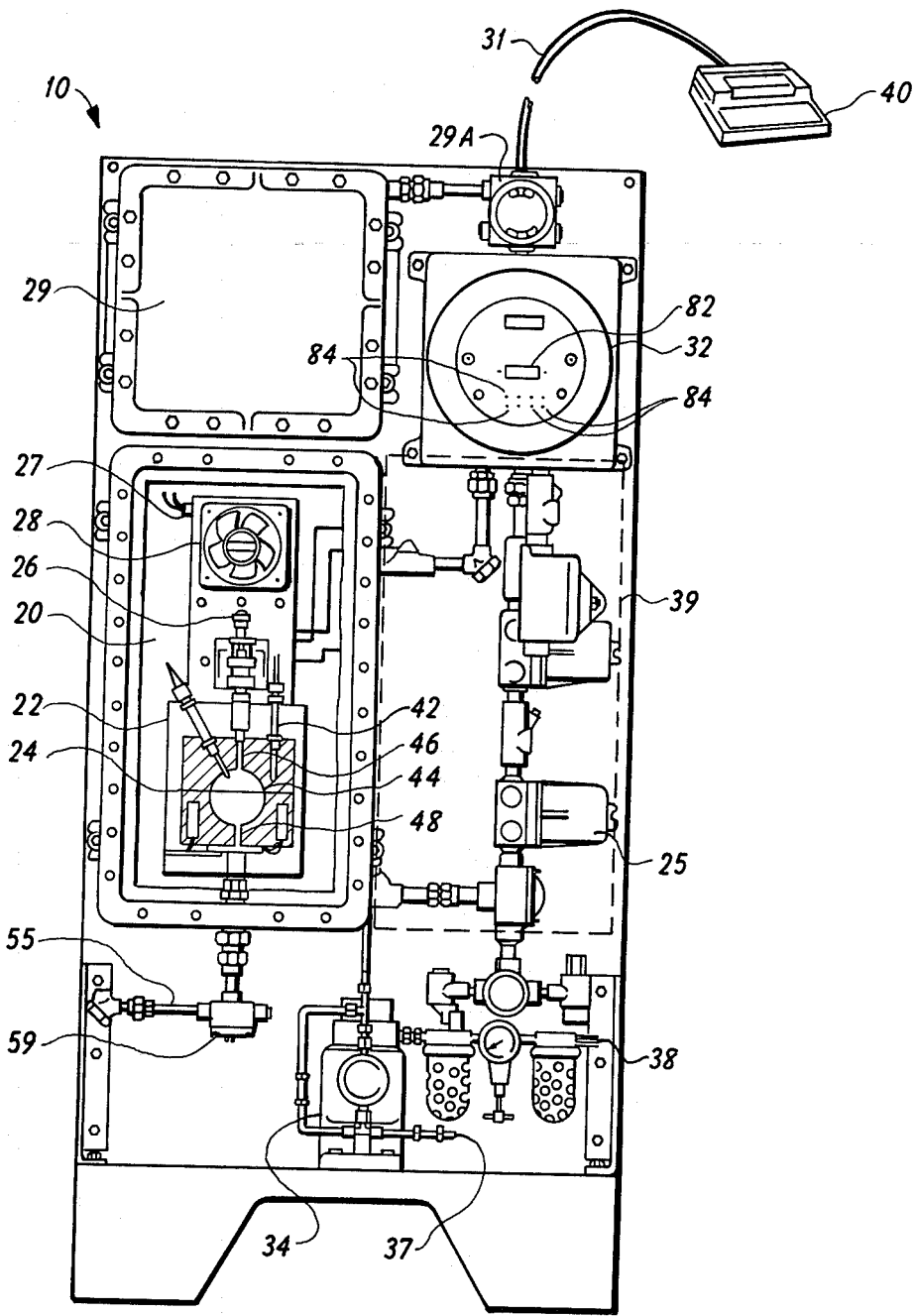
FIG. 1 is a front elevation view of an on-line, microprocessor controlled octane analyzer constructed in accordance with a preferred embodiment of the present invention shown coupled to an input/output data terminal.

Turning now to FIG. 1 of the drawings, a fully automatic, on-line process control octane analyzer 10 is shown to include an oven chamber 20 (illustrated with its cover removed) containing a reactor housing 22 and its associated reactor block 24, a sample injection valve 26, and a combination air heater/fan 28. The analyzer further includes an electronics housing 29 for a microprocessor 30 (see FIG. 5), a display panel 32 (again without its cover), and a gasoline sample pump 34 and its associated fuel inlet conduit 37 and air intake conduit 38. Though not specifically depicted a flow control panel is positioned to cover most of the piping and other electrical components and connecting conduits as indicated by a dashed line 39. Also shown coupled to the microprocessor via a cable 31 emanating from a junction box 29A at the side of the electronics housing is an input/output data terminal 40. The analyzer is a freestanding, environmentally secure unit adapted to be located in close proximity to a process stream in a refinery such that a bypass flow stream may be admitted to an inlet port (not shown) leading to the conduit 37 at the bottom of the analyzer.

Figure 2:
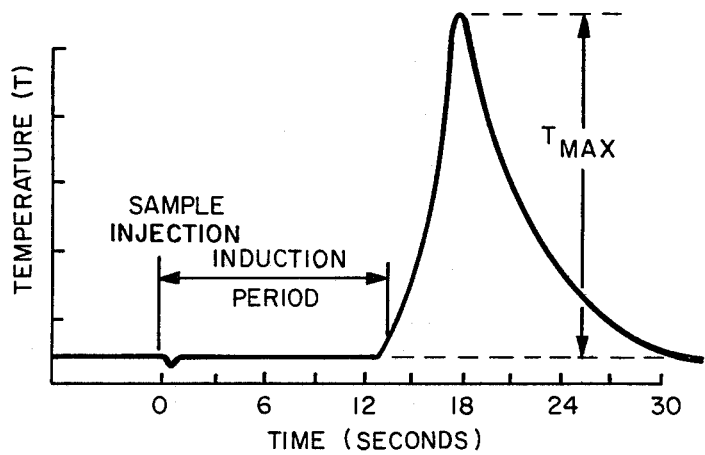
FIG. 2 is a graph of peak amplitude versus time to reach peak for a typical gasoline undergoing a cool flame reaction.

The method of analysis for the analyzer 10 is based on the phenomena of cool flame partial oxidation reactions which, as is well known, is one stage of fuel combustion generally occurring between 250° and 350° C. and capable of providing measurable parameters correlatable to octane number values. FIG. 2 represents a typical cool flame reaction for a fuel-air mixture. After a gasoline sample is injected into a heated reactor chamber, an induction period occurs prior to a sharp rise in temperature as the reaction begins. This exothermic reaction culminates in a well defined peak, the amplitude of which is representative of the severity of the reaction. As taught in the aforementioned U.S. Pat. No. 3,738,810, this peak height and the induction period represent parameters that are directly correlatable to octane number. For purposes of understanding the operation of the present invention in the context of this embodiment, the parameters of interest are the peak temperature amplitude and the time after sample injection in which this amplitude is reached at a particular reactor block temperature hereinafter referred to as "peak amplitude/time coordinates."

Figure 3:
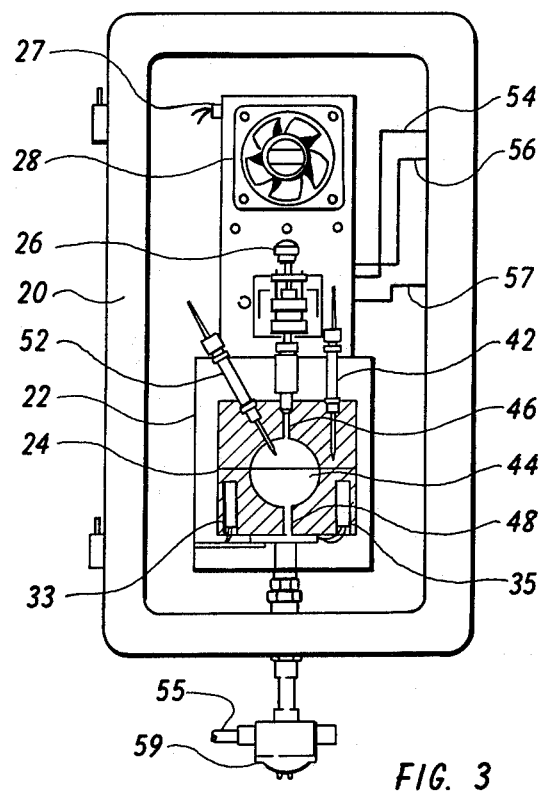
FIG. 3 is a front elevation view, partly in section, of the reactor housing for the embodiment of FIG. 1.
Figure 5:
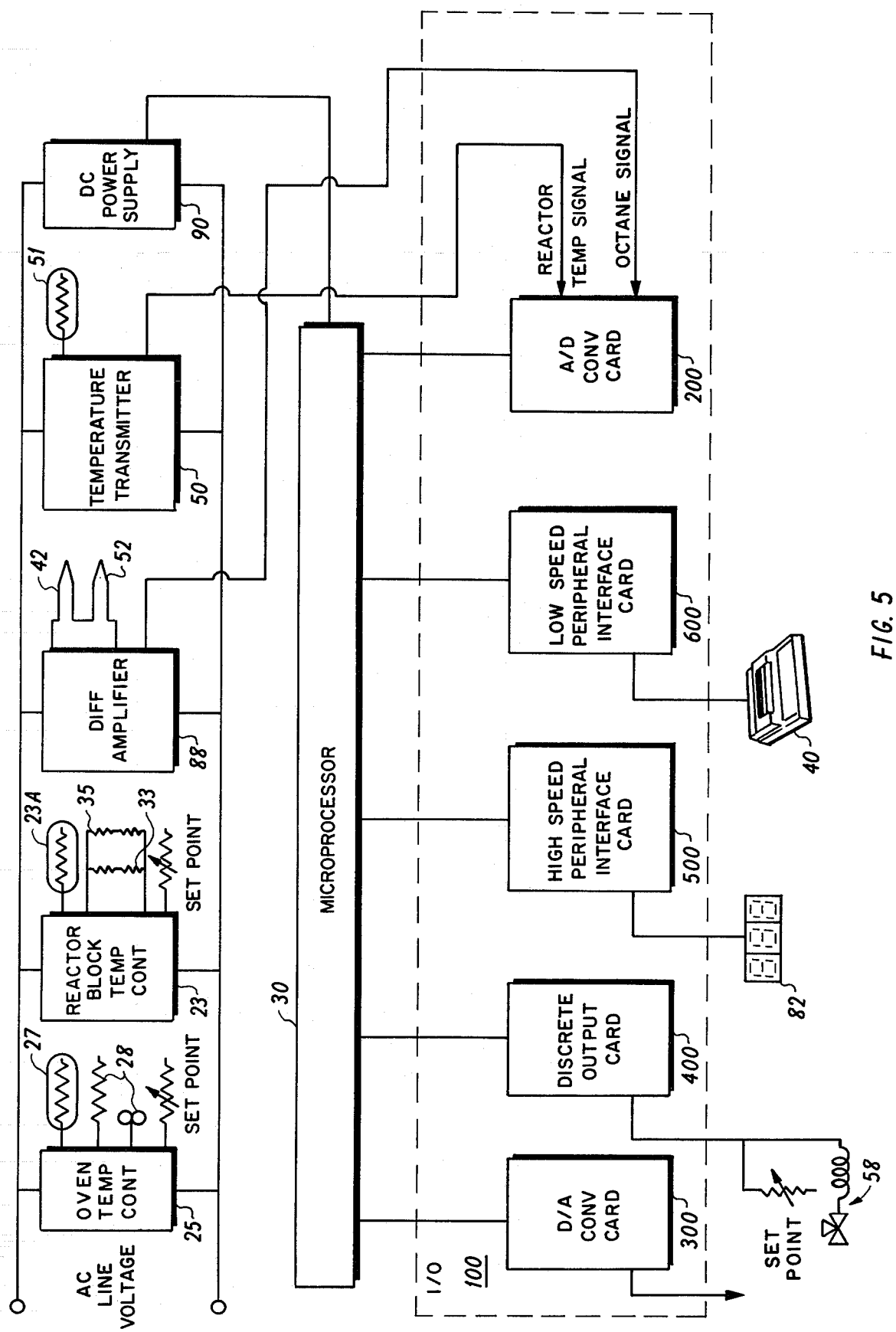
FIG. 5 is a block diagram of the electrical control system and its interface with the reactor assembly for the analyzer of FIG. 1.

FIG. 3 presents a more detailed view of the oven chamber 20. As previously noted this chamber is maintained at an elevated temperature of preferably 70° C. by the combination air heater/fan 28 under regulation by an oven temperature controller 25 (see FIG. 1) that receives temperature measurement inputs from a thermistor 27. The chamber thus assures that the gasoline sample and the reaction air supply are sufficiently preheated to maintain a constant fuel/air ratio to support the reaction. The reactor block 24, which is fixedly mounted in the cylindrical insulated housing 22, is separately heated by two pairs of symmetrically positioned electrical cartridge heaters 33, 35 (with only the heaters closest to the plane of the drawing figure shown) to about 300° C., the approximate midpoint of the cool flame reaction temperature zone. Referring now briefly also to FIG. 5, a platinum RTD probe 23A provides an appropriate signal to a reactor block temperature controller 23 which in turn produces a control signal to the cartridge heaters to appropriately regulate block temperature to the desired value.

Figure 4:
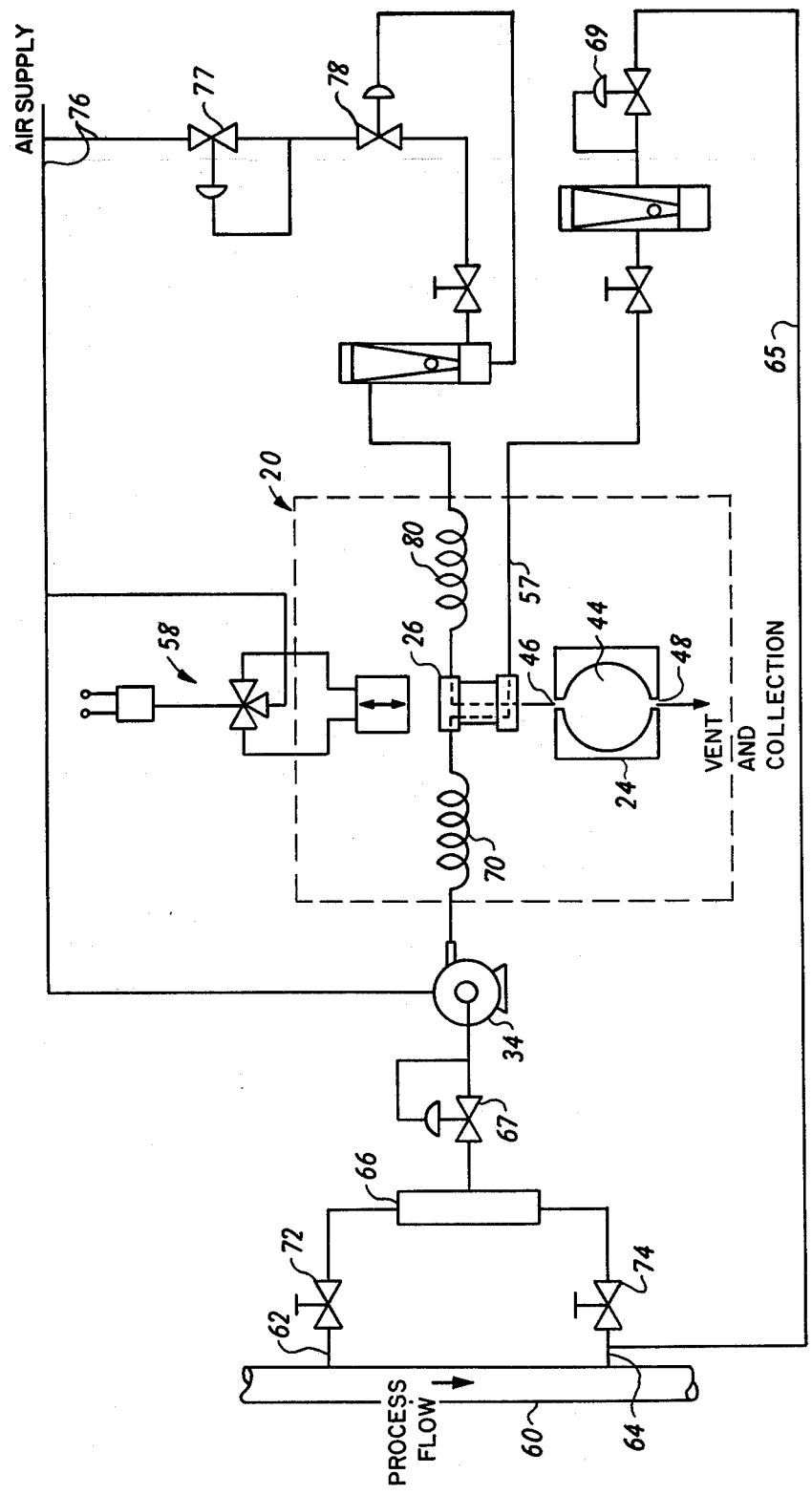
FIG. 4 is a schematic diagram of the fuel/air flow system for the analyzer of FIG. 1.

The reactor block 24 has an inner spherical cavity 44 at its center accessed by respective inlet and outlet ports 46, 48 in which the actual reaction occurs. Protruding slightly into the inner cavity is a measuring thermocouple 52 that determines the temperature rise therein due to the reaction. A reference thermocouple 42 imbedded in the block measures the temperature of the block. Reaction air and gasoline sample are inletted to the oven chamber 20 by a pair of conduits 54, 56 respectively. These conduits are fed to the sample injection valve 26 which is driven by a solenoid 58 (FIG. 4). Details of the operation and construction of this sliding sample valve, which permits a fixed volume of sample to be mixed with the flowing reactor air stream for injection into the reaction cavity 44, are well known to those of skill in the art. The valve is of the general type disclosed in U.S. Pat. No. 3,933,165 which may be referred to if further details are required. During periods when sample is not injected, a recycling flow is provided by means of a sample outlet conduit 57. To complete the oven chamber assembly, a drip pot 59 is located at the bottom of the chamber to collect non-gaseous waste products of the reaction and vent exhaust gases to the atmosphere through a vent pipe 55. For safety purposes, a flash-back arrestor (not shown) is inserted at the exit of the outlet port 48.

Turning now to FIG. 4, a schematic representation depicts how the analyzer is "tied" into a typical process stream of a refinery. Gasoline flowing through a main conduit 60 is tapped off by a pair of by-pass conduits 62, 64 through associated bypass valves 72, 74 and fed into an in-line fuel filter 66. Although only a single filter is shown schematically, it is well understood that a series of filters is normally placed along strategic points of the gasoline stream both prior to entering as well as within the analyzer to assure sample purity. The stream leaving the filter is lowered in pressure by a reducing regulator 67 and routed to the air driven gasoline sample pump 34. At this stage, the fuel sample is recompressed to approximately 60 psi by appropriate manipulation of a back pressure regulator 69 located on the outlet side of the sample injection valve 26. The pump is driven at a rate of speed so as to set the flow of gasoline sample at 5 ml per minute. During the vast majority of the analyzer cycle time the valve is not actuated, and sample, after being heated by a heat exchanger 70, is caused to bypass the reactor cavity inlet port 46 and flow through the sample outlet conduit 57 for recycling along a reflow conduit 65.

As shown at the end of the schematic opposite the process stream, air is admitted to the analyzer from a supply source (not shown) and distributed within the analyzer by means of a pneumatic conduit 76. After suitable regulation by a pressure regulator 77 and a flow controller 78, and heating by an exchanger coil 80, this air supply is passed to the sample injection valve 26 where it is caused to continuously flow through the reactor cavity 44 at a rate of about 70 cc per minute. Thus in effect the air supply serves as both the carrier gas for transporting the liquid sample to the volatilization and reaction zones as well as the medium for supporting oxidation.

The normal cycle time for an analysis run is five minutes, that is, once every five minutes the microprocessor 30 sends a command signal to the solenoid 58. This, of course, causes reciprocating sliding movement of the injection valve 26 thereby allowing a 12 microliter aliquot to be mixed with the flowing air stream, volatilized, conducted into the reactor inlet port 46 and shortly thereafter into the reactor cavity 44 to support the cool flame reaction. A three-digit LED display 82 located on the display panel 32 is driven by the microprocessor and charts the elapsed cycle time. This display panel also includes a series of manually actuatable switches 84 which can override the automatic cycling controlled by the processor. However, these switches are primarily for maintenance purposes and are not important for an understanding of the present invention, and accordingly will not be discussed further.

Considering in more detail the operation of the analyzer and especially that of the electronic control circuitry interfacing with the oven chamber 20, FIG. 5 depicts an electrical schematic for the overall analyzer which, as shown, is powered from a-c line voltage. For consistency, the same reference numerals have been adopted to indicate parts identical to those shown in the preceding drawings. At the heart of the system is the microprocessor 30 which receives its operating power from a d-c power supply 90. The microprocessor is an 8-bit device commercially available from Motorola, Inc. as Model 6802. The processor includes both read only memory (ROM) and random access memory (RAM) logic units as well as the usual computational logic elements. Additionally, interface to and from the processor is accomplished through a series of input/output (I/O) circuitry indicated generally by the reference numeral 100. These I/O circuits include an analog to digital (A/D) converter 200 for accepting analog inputs such as reactor temperature and measurement signal; a digital to analog (D/A) converter 300 for producing an analog output control signal; a discrete output card 400 for producing outputs to energize the solenoid 58 as well as establishing the set point for the reactor block temperature controller 23; a high-speed peripheral interface card 500 for driving the LED display 82; and a low-speed peripheral interface card 600 for communicating with the input/output data terminal 40. Primary operator interface with the microprocessor is through the keyboard of the input/output data terminal which in this the preferred embodiment is a Texas Instruments, Inc. Model 743KSR terminal. The terminal thus initiates an analysis after the reactor block 24 has stabilized at the appropriate temperature; it also has the capability of selecting various measurement range values if such an option is desired. Of course, the terminal prints a copy of test results and related useful information.

The operation of the electronic control circuitry in support of an analysis run is as follows. First a check is made to assure that the reactor block 24 is being precisely maintained at the desired temperature value. This is accomplished by providing as an input to the microprocessor 30 through the A/D converter 200 a temperature signal from a temperature transmitter 50 indicative of the reactor block temperature. Because of the criticality of the block temperature measurement, it is desirable to monitor the performance of the reactor block temperature controller 23 through the microprocessor by an independent temperature signal from a separate RTD sensor 51 adjacent the temperature transmitter. Deviations outside specified limits result in alarm conditions being audibly sounded on the terminal 40. Temporary variances, as resulting during startup or between analyses run at different block temperatures, between the set point value and the measured value are controlled by the block temperature controller 23. Set point selection is handled by the microprocessor which sends an appropriate output signal via the discrete output logic card 400. Utilizing precision RTD sensors and heaters in conjunction with independent temperature monitoring allows this temperature to be reliably controlled to $\pm 0.1°$ C.

The operation of the block temperature control mechanism is to be contrasted with that of the oven temperature control circuitry which is not that closely controlled. Instead the thermistor 27 located near the top of the oven chamber 20 (and external to the reactor housing 22) serves as an input signal to the oven temperature controller 25. Oven temperature is then regulated to within 1° C. by suitable adjustment of the finned heater/convection fan combination 28. As previously mentioned, the purpose of maintaining an elevated oven temperature is primarily to keep the fuel/air ratio constant before entering the volatilization zone of the reactor cavity 44.

Shortly after sample injection, the cool flame reaction begins as signified by an increase in reactor temperature. The temperature rise due to the reaction is detected by the measuring thermocouple 52, which together with the temperature signal from the reference thermocouple 42 are inputs to a differential amplifier 88. The output of this amplifier is an input through the A/D converter 200 to the microprocessor 30. The processor updates its memory every 100 ms with this temperature value and is thus able to rapidly determine the occurrence of a peak slope change which represents as shown in FIG. 2 the peak amplitude and hence the octane signal. At that point, the magnitude (temperature) of the peak amplitude and the time after sample injection to reach the peak as read from the system operating clock are stored in memory for later retrieval. The microprocessor can also produce a digital value corresponding to the octane number so determined, feed this value to the D/A converter 300 and ultilize it as a 4–20 ma control signal for an on-line blender. Further discussion of this option will be deferred until later.

To briefly summarize at this point the operation of the analyzer and its interaction with a process stream, a gasoline sample is withdrawn from the main flow conduit 60, pressure regulated, temperature controlled and pumped to the sample injection valve 26. Meanwhile the reactor air supply from a pneumatic source of supply is pressure regulated, flow and temperature controlled and passed continuously through the injection valve to the internal reactor cavity 44. The reactor block 24 is heated to the desired temperature for precipitating the cool flame reaction (e.g., 300° C.) and is tightly controlled to maintain the selected temperature. The temperature inside the oven chamber 20 surrounding the reactor housing 22 is also elevated and controlled primarily for the purpose of temperature controlling the fuel and air as mentioned above, but not as precisely as the reactor block temperature. Once every five minutes upon command from the microprocessor 30 the solenoid 58 is actuated causing the injection of a precise volume of sample into the reactor cavity where it is mixed with the reactor air supply to produce a cool flame reaction. The measuring thermocouple 52 responds to this exothermic reaction and because of its differential connection with the reference thermocouple 42, a final output signal is generated and stored indicative of the severity of the reaction and hence the octane number. During operation this cycle is repeated every five minutes whether for performing measurement analyses or calibrations.

Having thus described the principle of operation of the major components of the analyzer and its on-line interface capabilities with the process in considerable detail, the techniques for octane analysis in accordance with the present invention will now be discussed. Prior techniques have preferably involved a "pre-calibration" procedure wherein known samples (octane number and composition) of the type anticipated to be analyzed are run through an analyzer over a desired, limited operating range. For example, in the past if it were desired to analyze primary reference fuels (PRF) over a research octane number (RON) range from 95 to 100 RON, three known PRF samples would be selected, e.g., 95 RON, 97.5 RON and 100 RON. (It should be noted that the composition of PRF fuels having various RON values is precisely known and may be found, for example, in ASTM Manual No. D-2699.) The reactor block temperature would then be adjusted over a series of analyses until an approximately linear response is achieved as disclosed in the aforementioned U.S. Pat. No. 3,738,810. This particular temperature is then selected for all future analysis runs involving the particular fuel of interest. The difficulty with such an approach is that if within that preset octane span (i.e., 95 to 100 RON) a greatly different composition fuel such as a toluene check fuel (TCF) is run through the analyzer, the analyzer will generate incorrect data because its response will not correspond to the calibrating fuel used, a PRF for this case.

The present invention overcomes such shortcomings by recognizing that an important factor in the analysis of octane number is to achieve an optimum point of the reaction, which in this example is the peak amplitude of the severity of reaction, and the time involved to reach the peak. These two measurable parameters can be combined to find an optimum operating point that can be utilized to produce a composition/RON plot inside the domain of which lie an infinite number of peak amplitude/time coordinates the values of which represent RON and composition information for unknown samples. The recognition of this factor was the consequence of repetitively measuring peak amplitude temperatures and the time to reach peak at many different reactor block temperatures for different fuels of varying, but known beforehand, compositions and RON values. Results of this analysis work and an understanding of their significance are provided in FIGS. 6–8 together with the accompanying written disclosure.

Figure 6:
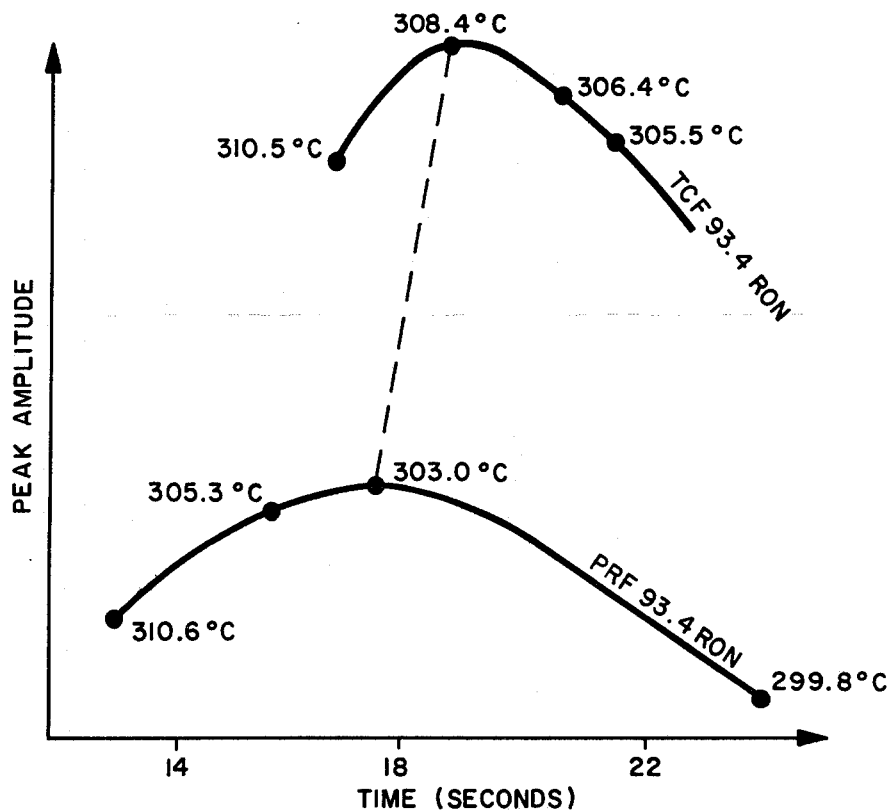
FIG. 6 is a plot of a series of peak amplitude temperatures versus time to reach peak as a function of reactor block temperature for two fuels of equal octane number but varying aromatic content.

FIG. 6 is a graph of peak amplitude/time coordinates for a TCF and a PRF both of 93.4 RON plotted as a function of temperature and time. This is the result of cycling the known samples through a range of reactor block temperatures, determining the length of time to reach a maximum peak for a given reactor temperature, and forming a composite plot of these peak amplitude/time coordinates as a function of reactor block temperature where the RON of the sample is constant. Included as the lower graph of FIG. 6 is a composition plot for the sample of the PRF of 93.4 RON. From the graph it can be seen that the maximum peak amplitude/time coordinate occurred at approximately eighteen seconds after sample injection and at a reactor block temperature of 303° C. In accordance with the embodiment being described, this temperature represents the optimum point of the reaction. It is believed that the optimum point represents a condition where a maximum of the fuel components is oxidized. Preconditioning the reactor block in this manner provides an important foundation for future analyses as will be discussed presently.

It is also apparent at when the RON remains constant but the composition of the fuel varies a new optimum temperature exists and is found by varying the reactor block temperature in accordance with the procedures outlined above. However, once determined, this optimum point is constant for that particular composition. The upper graph of FIG. 6 gives the results of analyses run with a TCF of the same RON value as the PRF fuel depicted in the lower graph. It will be observed that under these conditions the TCF results in a more severe reaction and the optimum temperature point has been shifted upward both in terms of time to reach peak amplitude and reactor block temperature. The slope of the line joining the optimum point for both fuels thus represents a specific value of constant RON's, that is to say any unknown fuel whose optimum point coincides with this specific slope will have an RON of 93.4. The length of this line can be scaled to provide a composition index.

Figure 7:
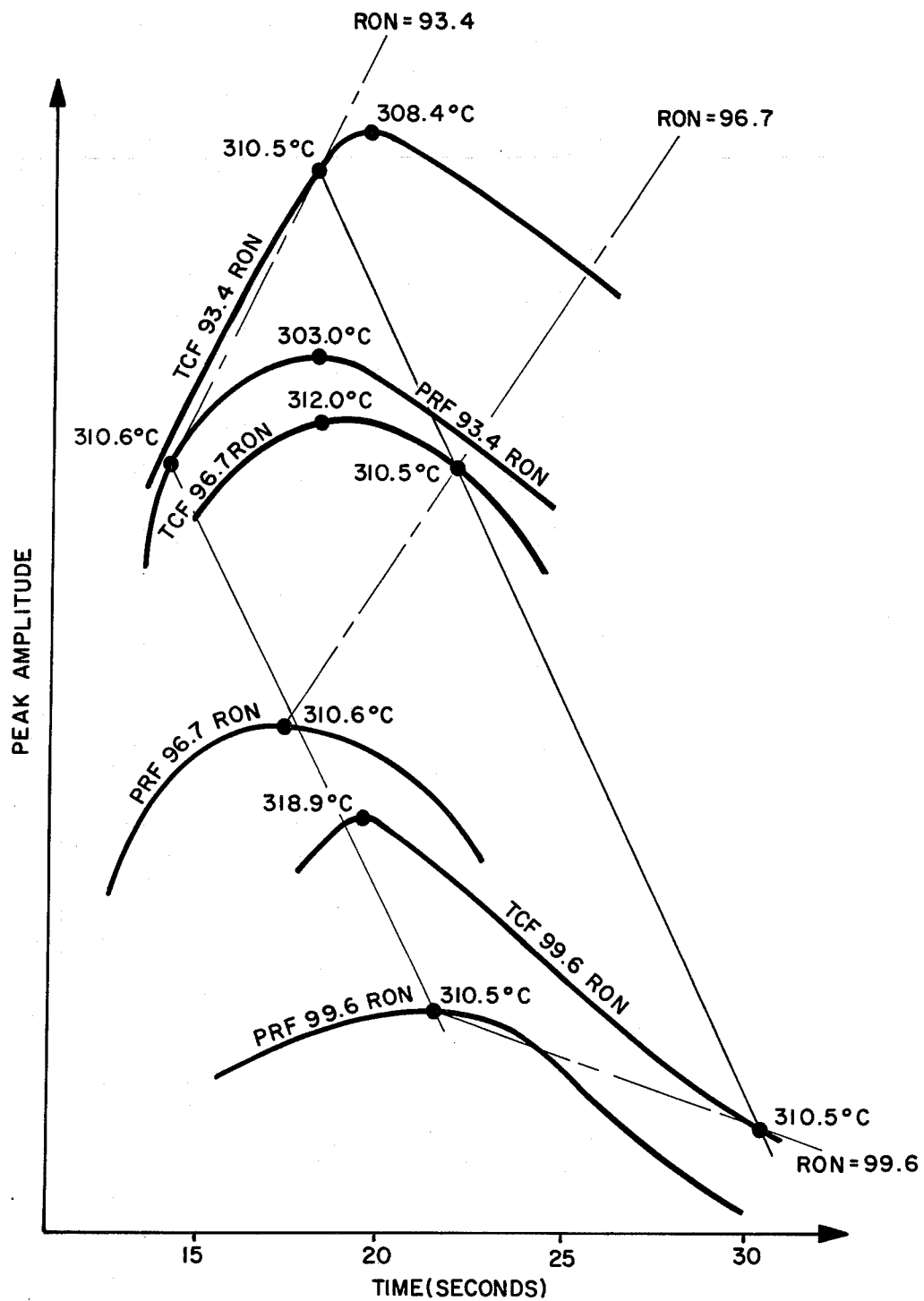
FIG. 7 is a plot similar to that of FIG. 6 only amplified to include a range of octane number fuels and compositions.

However, from a commercial standpoint the observations with respect to the graphs of FIG. 6 may not be fully desirable to implement because this necessitates using a temperature programmable reactor assembly. Nonetheless, these discoveries are still significant and as illustrated in the expanded plot of FIG. 7 useful in establishing the composition/RON matrix mentioned previously. FIG. 7 shows a series of plots similar to those shown in FIG. 6 only expanded to show TCF's and PRF's at three different RON values: 93.4, 96.7 and 99.6. To avoid having to vary reactor block temperature to account for shifts in the optimum point from sample to sample, this composite plot and that of FIG. 9 demonstrate that if the optimum reactor block temperature for the target fuel (the midpoint of the RON span—96.7) is chosen to perform analysis runs on other known samples, and if the RON span is not too large, near optimum results will be achieved. In other words, the resultant vectors drawn through equal reactor block temperature points between different samples sufficiently characterize the output of the reaction so as not to detract from practical measurement results. Thus, the dashed lines in FIG. 7 represent equal block temperature conditions between two different composition fuels of constant RON value and the thin solid lines represent equal block temperature points between the same composition fuels but having different RON values. Thus, any unknown fuel whose peak amplitude/time coordinate falls on the slope of a dashed vector has an RON value equal to that vector and a composition intermediate the composition represented by the two end points of this vector. Correspondingly, an unknown falling on the solid vector has the same composition as that vector and an RON value between the end points.

Figure 8:
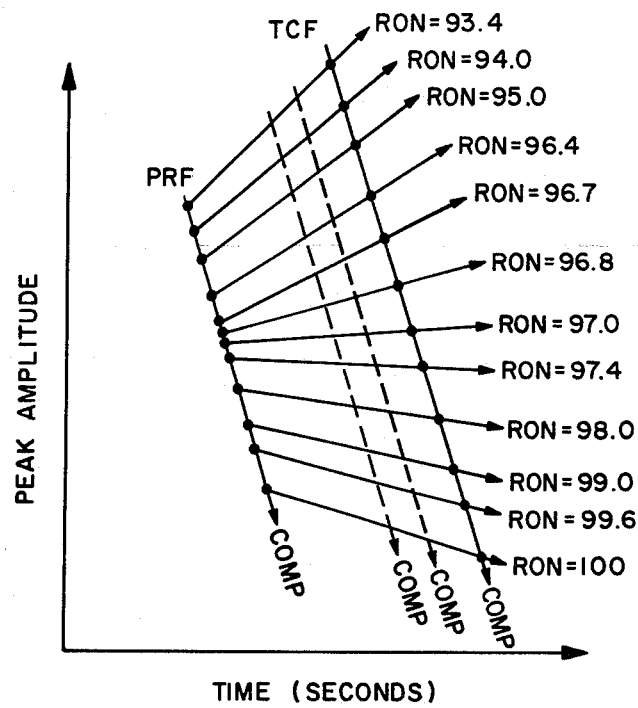
FIG. 8 is a plot derived in part from the data presented in FIG. 7 wherein equal reactor block temperature points have been connected by a series of straight lines to form a matrix of equal block temperature values.

FIG. 8 is a composite graph derived from the observations made with respect to FIGS. 6 and 7 in which equal reactor block temperature points between different composition fuels of the same octane number and similarly equal reactor block temperature points between fuels of the same composition but varying octane number have been joined by a series of lines to produce a multi-dimensional matrix of peak amplitude/time coordinates, the outline of which appears trapezoidal. In other words a functional mapping has been achieved between peak amplitude/time coordinates and octane number and composition with the RON and composition value of any such coordinate falling within this domain being uniquely determinable. As can be appreciated, from a theoretical point of view the boundaries of this domain are only limited by the extent of the number of sample analyses run before unknown samples are introduced into the analyzer; however, span limits of 6–8 octane numbers are more practical in the design of a commercially viable analyzer to meet specified accuracy and repeatability requirements of the output signal. It is presently contemplated that the determination of RON value will be of primary commercial significance, and thus perhaps three to five known samples of varying RON value will be run through the analyzer to set up the domain boundaries. RON values in between these measured values can be linearly interpolated and still meet desired accuracy requirements.

Figure 9:
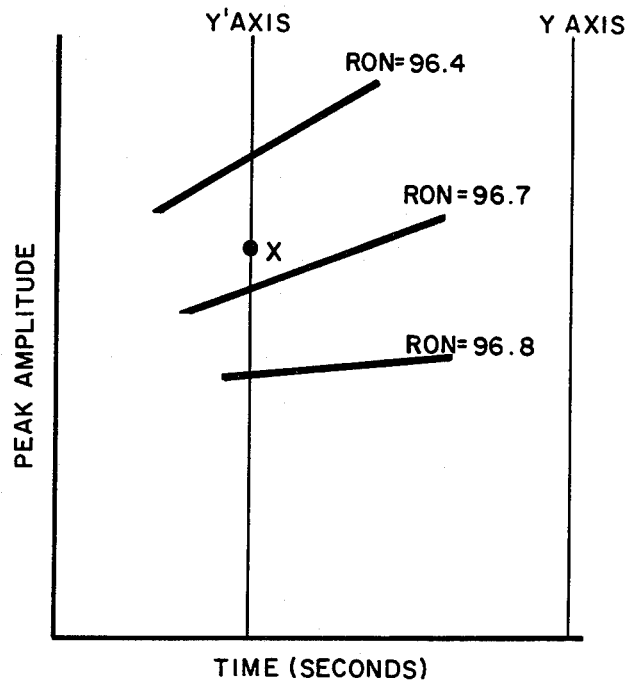
FIG. 9 is an exemplary plot showing a portion of an equal block temperature value plot similar to the type depicted in FIG. 8 demonstrating how the octane number of an unknown sample may be determined.

FIG. 9 amplifies a portion of the equal reactor block temperature plot of FIG. 8 demonstrating the ease and accuracy with which unknown RON values can be obtained. Because the span of RON values can be finely divided, the short distance between adjacent slopes can be essentially treated as being linear without sacrificing accuracy. Then intermediate values can be assigned to adjacent RON vectors and points in between can be pinpointed using Cartesian coordinate fundamentals. Although the matrix may be derived with and unknown values calculated by manual graphic techniques, it is preferred that this be done utilizing the capabilities inherent in the microprocessor. The microprocessor has stored in its memory digital values representing the slopes of the derived RON values as well as values to generate an imaginary y axis to the right of the trapezoidal matrix onto which the RON value vectors are projected. The points of intersection of these vectors with the y axis are not usually equally distributed, hence the octane value between adjacent RON value vectors may be small while that of another pair may be larger. Thus when an unknown peak amplitude/time coordinate (designated as "x") value is inputted to the microprocessor, the processor performs in parallel a series of iterations to determine which RON value vector intersecting the y axis is closest to point x and whether x is above or below this vector. This step thus determines which of the known RON values x is between. Next the imaginary y axis is back projected to coincide with the unknown point and a new imaginary y' axis is generated with rescaled digital values being calculated between the new intercept points of the prior-determined adjacent RON value vectors on this y' axis. Hence the exact location of point x in the coordinate system is pinpointed with the percent difference between the two known RON value vectors representing the RON value of unknown point x. In similar fashion values along the x axis of the matrix can be scaled to provide a signal indicative of the composition of the unknown sample. Implementing such a procedure in a programmable read-only memory is straightforward and well understood by those of skill in the art of microprocessor design and may be readily accomplished by such a skilled artisan.

Figure 10:
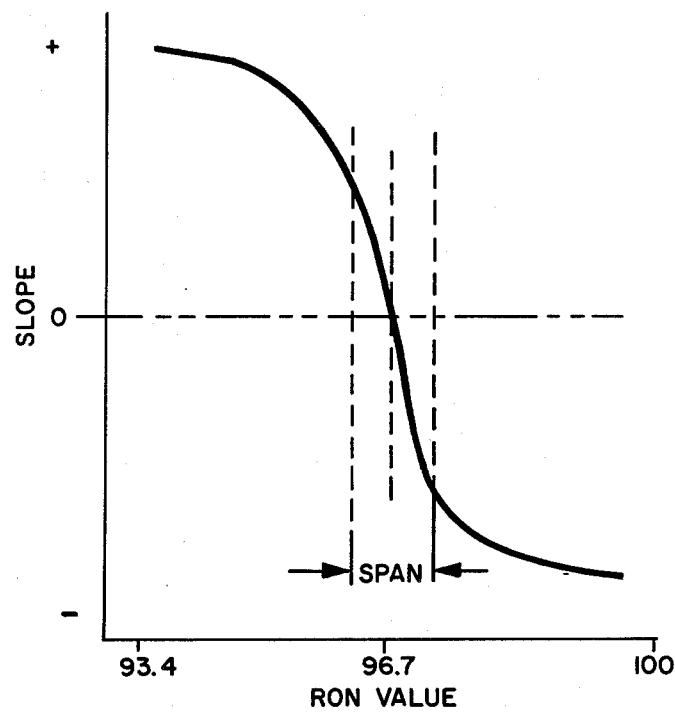
FIG. 10 is a graph showing that the octane number output value of the analyzer can be readily utilized as an input control signal for an on-line blending operation.

FIG. 10 represents a graph of the slopes shown in FIG. 8 versus RON value over the range shown in FIG. 8. It is apparent that around the target-control point (mid-point of RON span) increased sensitivity exists. Thus if it is desired to provide a control signal to an automatic blender about the target point (e.g., 96.7 RON), control operation is being conducted in the linear and steepest portion of the curve resulting in the generation of a 4–20 ma signal, for example, that will produce on-line control to greater than 0.1 RON number.

Although a preferred embodiment has thus been disclosed in detail, this is for illustrative purposes only as modifications will become apparent to those of ordinary skill in the art. For example, the optimum point has been described throughout as a combination of peak amplitude, time to reach peak amplitude and reactor block temperature parameters. However, it is also possible to utilize other measurable values to determine the optimum point, for example, the pressure front developed as a result of the cool flame reaction, the fuel/air ratio, the volume of fuel or air used, and the positioning of measurement devices. Such modifications and any other similar deviations are not to be considered as falling outside of the scope of the present invention, nor should any details provided in this illustrative embodiment be considered limitations to the invention as defined in the accompanying claims.

I claim:
1. A method of determining the value of a desired characteristic of a hydrocarbon substance comprising the steps of:

injecting a known hydrocarbon substance into a reaction cavity of a reactor block;

reacting said substance with a gas at a known reactor block temperature so as to undergo a cool flame reaction within said cavity;

measuring at least two parameters relating to said cool flame reaction that are each correlatable with the value of said desired characteristic;

varying the reactor block temperature about said known temperature and then repeating the steps above to determine an optimum point for said reaction where a maximum of the fuel components is oxidized during said reaction;

controlling subsequent cool flame reactions with different, known hydrocarbon substances at or near said optimum point to develop a plurality of measured values corresponding to said two parameters;

mapping said measured values onto a multi-dimensional matrix whose array include said two parameters such that a coordinate point in the domain of said matrix is uniquely correlatable to said desired characteristic;

subsequently performing at said otimum point a cool flame reaction on an unknown hydrocarbon substance to yield a measured value correlatable with said matrix; and correlating said measured value of said unknown hydrocarbon substance with said matrix to determine the value of said desired characteristic of said unknown hydrocarbon substance.

2. The method of claim 1 wherein peak temperature amplitudes and the time to reach peak for each analysis of known hydrocarbon substances are measured to determine a plurality of reaction peak temperature amplitudes versus time to reach peak points and including the step of correlating the peak temperature amplitude and the time to reach peak for said unknown hydrocarbon substance with said matrix.

3. The method of claim 2 wherein said optimum point represents the temperature of said reactor block at which the maximum peak temperature amplitude versus time to reach peak of the reaction occurs.

4. The method of claim 1 wherein said hydrocarbon substance is gasoline and said desired characteristic is either octane number or an indication of the composition of said gasoline.

5. The method of claim 4 wherein said gas is air continuously supplied at a constant flow rate through said reaction cavity and wherein a fixed volumetric sample of said gasoline is periodically injected to mix with said air prior to entering said cavity.

6. The method of claim 1 wherein said known hydrocarbon substances are gasolines of predetermined composition and octane number, said two parameters are the reaction peak temperature amplitude and the time to reach peak, and said two parameters being interconnected within said matrix such that points of equal reactor block temperatures between substances of the same octane number, but different composition and correspondingly of different octane number and similar composition serve to define said matrix in terms of composition and octane number values.

7. The method of claim 6 wherein within said matrix the lines joining points of equal block temperature of same octane number substances represent a value of a specific, constant octane number and the lines joining points of equal block temperatures of said composition substances represent a value of a specific composition.

8. The method of claim 6 including the steps of storing a series of digital values corresponding to the slopes of lines formed by interconnecting said equal reactor block temperature points between samples of the same octane number in a memory means of a digital processor;

providing to said processor an input signal representative of a coordinate of peak severity amplitude versus time to reach peak of an unknown sample;

computing within said processor the location of said coordinate within said matrix to provide a value of said desired characteristic.

9. The method of claim 8 wherein said desired characteristic is octane number and including the further step of producing an analog output control signal representative of the octane number of said unknown sample.

10. A method of performing octane number analysis on an unknown sample of gasoline comprising the steps of:

injecting a fixed volume of a sample fuel whose composition and octane number are known together with a combustion-supportible carrier gas into a reactor block to produce a cool flame reaction therein;

detecting both the peak temperature rise of said cool flame reaction and the time to reach peak;

varying the temperature of said reactor block and repeating the steps above to find the optimum reactor block temperature defined by that block temperature which produces a maximum peak temperature rise for said sample fuel;

determining a matrix of octane number and composition values by:

(a) repeating the above steps of injecting and detecting for samples of other known fuels of different octane number and composition at said optimum temperature, to develop a plurality of data points, each of said data points corresponding to both said peak temperature rise and the time to reach peak, (b) interconnecting data points between samples of the same octane number, but different composition, the slopes of the lines joining said data points defining in one dimension a range of octane number values, and (c) interconnecting data points between samples of the same fuel composition, but different octane number, the slopes of the lines joining said data points defining a range of fuel composition values; and performing an analysis on an unknown fuel sample at said optimum temperature and comparing its peak temperature rise and time to reach peak parameters to said matrix values to determine either the octane number or composition of said unknown fuel sample.

11. The method of claim 10 including the steps of:

providing as an input to a microprocessor an octane signal representative of the severity of said cool flame reaction from the output of a differential amplifier whose inputs are the temperature rise of said reaction and the temperature of said reactor block;

determining the time at which the maximum temperature rise occurred and storing a digital value indicative of said time in memory means of said microprocessor;

storing in said memory means a series of digital values corresponding to said matrix values; and computing in said microprocessor a numerical value corresponding to said octane signal.

12. The method of claim 11 including the step of producing an analog output signal indicative of said octane signal.

* * * * *